(12) United States Patent
Bessler et al.

(10) Patent No.: US 9,888,922 B2
(45) Date of Patent: *Feb. 13, 2018

(54) NATURAL ORIFICE BARIATRIC PROCEDURE AND APPARATUS FOR USE THEREWITH

(71) Applicant: Covidien LP, Mansfield, MA (US)

(72) Inventors: Marc Bessler, Teaneck, NJ (US); Robert DeSantis, San Jose, CA (US); Stanislaw Marczyk, Stratford, CT (US)

(73) Assignee: COVIDIEN LP, Mansfield, MA (US)

( * ) Notice: Subject to any disclaimer, the term of this patent is extended or adjusted under 35 U.S.C. 154(b) by 299 days.

This patent is subject to a terminal disclaimer.

(21) Appl. No.: 14/690,655

(22) Filed: Apr. 20, 2015

(65) Prior Publication Data

US 2015/0238341 A1 Aug. 27, 2015

Related U.S. Application Data

(63) Continuation of application No. 13/472,836, filed on May 16, 2012, now Pat. No. 9,034,003, which is a continuation of application No. 12/272,846, filed on Nov. 18, 2008, now Pat. No. 8,192,448.

(60) Provisional application No. 61/003,820, filed on Nov. 19, 2007.

(51) Int. Cl.
*A61B 17/068* (2006.01)
*A61B 17/072* (2006.01)
*A61B 17/28* (2006.01)
*A61F 5/00* (2006.01)

(52) U.S. Cl.
CPC ...... *A61B 17/068* (2013.01); *A61B 17/07207* (2013.01); *A61B 17/2812* (2013.01); *A61F 5/0076* (2013.01); *A61F 5/0083* (2013.01)

(58) Field of Classification Search
CPC ............ A61B 17/068; A61B 17/07207; A61B 17/115; A61B 17/1152; A61B 17/1155; A61B 17/1157; A61B 17/2812; A61F 5/0076; A61F 5/0083; A61F 5/0086; A61F 5/0089
USPC ........ 606/153, 111, 114–115, 128, 119, 127, 606/139, 144; 128/898; 227/175.1–182.1
See application file for complete search history.

(56) References Cited

U.S. PATENT DOCUMENTS

| 4,328,805 | A | 5/1982 | Akopov et al. |
| 5,297,536 | A | 3/1994 | Wilk |
| 5,458,131 | A | 10/1995 | Wilk |
| 5,653,374 | A | 8/1997 | Young et al. |
| 6,953,139 | B2 | 10/2005 | Milliman et al. |
| 8,192,448 | B2 * | 6/2012 | Bessler ............ A61B 17/07207 227/175.1 |
| 9,034,003 | B2 * | 5/2015 | Bessler ............ A61B 17/07207 606/153 |
| 2003/0236549 | A1 | 12/2003 | Bonadio et al. |

(Continued)

*Primary Examiner* — David C Eastwood

(57) ABSTRACT

A method of performing a bariatric procedure through a natural body orifice is disclosed. The method comprises the step of providing a surgical instrument, comprising a handle portion, an elongated portion extending distally from the handle portion, and an end effector disposed adjacent a distal end of the elongated portion. The method also comprises the steps of inserting the surgical instrument through a natural body orifice of a patient such that the end effector is adjacent a portion of the patient's stomach, and using the surgical instrument to perform a surgical task.

15 Claims, 4 Drawing Sheets

(56) References Cited

U.S. PATENT DOCUMENTS

2004/0006351 A1   1/2004   Gannoe et al.
2004/0092974 A1   5/2004   Gannoe et al.
2006/0200004 A1   9/2006   Wilk
2006/0241344 A1   10/2006   Wilk
2006/0241570 A1   10/2006   Wilk
2009/0264808 A1   10/2009   Young

* cited by examiner

NATURAL ORIFICE BARIATRIC PROCEDURE AND APPARATUS FOR USE THEREWITH

CROSS-REFERENCE TO RELATED APPLICATIONS

This application is a continuation of U.S. patent application Ser. No. 13/472,836 filed May 16, 2012, which is a is a continuation of U.S. application Ser. No. 12/272,846 filed Nov. 18, 2008, which claims the benefits of and priority to U.S. Provisional Patent Application No. 61/003,820 which was filed on Nov. 19, 2007, the entire contents of which is hereby incorporated by reference in its entirety.

BACKGROUND

The present disclosure relates to performing a bariatric procedure through a natural bodily orifice and apparatus for use therewith. More particularly, the present disclosure relates to performing a sleeve gastrectomy (e.g., a vertical sleeve gastrectomy), for example, transvaginally and/or transrectally and apparatus for use to perform such a procedure.

A vertical sleeve gastrectomy is a restrictive form of weight loss surgery in which approximately 85% of the left side of the stomach is removed leaving a cylindrical- or sleeve-shaped stomach with a capacity ranging from about 60 cubic centimeters to about 150 cubic centimeters. A vertical sleeve gastrectomy results in a remodeled stomach that resembles the size and shape of a banana (FIG. 1 schematically illustrates the result of a vertical sleeve gastrectomy). Unlike many other forms of bariatric surgery, the outlet valve and the nerves to the stomach remain intact and, while the stomach is drastically reduced in size, its function is preserved.

Sleeve gastrectomies are typically performed through a patient's abdominal cavity. Several different ports are commonly provided to allow the surgeon to gain access through the patient's abdominal wall to reach the patient's stomach. There are typically a minimum of four ports that are generally used for this procedure (e.g., a stapler port, a grasper port, an endoscope port and an insufflation port). Additionally, a fifth port (e.g., an enlarged umbilical port) is often used for removal of a portion of the stomach. As can be appreciated, this method of performing a bariatric procedure leaves the patient with multiple visible scars.

To help prevent visible scarring from occurring during different types of surgical procedures, natural orifice transluminal endoscopic surgery (NOTES) techniques have been developed. The procedure of the present disclosure is a NOTES procedure where a surgical instrument is inserted through and penetrates the patient's vaginal orifice and/or rectal orifice to access the patient's stomach without penetrating the patient's abdominal wall.

SUMMARY

The present disclosure relates to a method of performing a bariatric procedure through a natural body orifice. The method comprises the step of providing a surgical instrument, comprising a handle portion, an elongated portion extending distally from the handle portion, and an end effector disposed adjacent a distal end of the elongated portion. The method also comprises the steps of inserting the surgical instrument through a natural body orifice of a patient such that the end effector is adjacent a portion of the patient's stomach, and using the surgical instrument to perform a surgical task.

The present disclosure also relates to a method of performing a transvaginal bariatric procedure. The method comprises the step of providing a surgical instrument comprising a handle portion, an elongated portion extending distally from the handle portion; and an end effector disposed adjacent a distal end of the elongated portion. The method also includes the steps of creating an incision in the vaginal wall, inserting a sealing device through the incision, insufflating the abdominal cavity, inserting the surgical instrument through the sealing device, and using the surgical instrument to perform a bariatric procedure.

DETAILED DESCRIPTION

Figure 1:
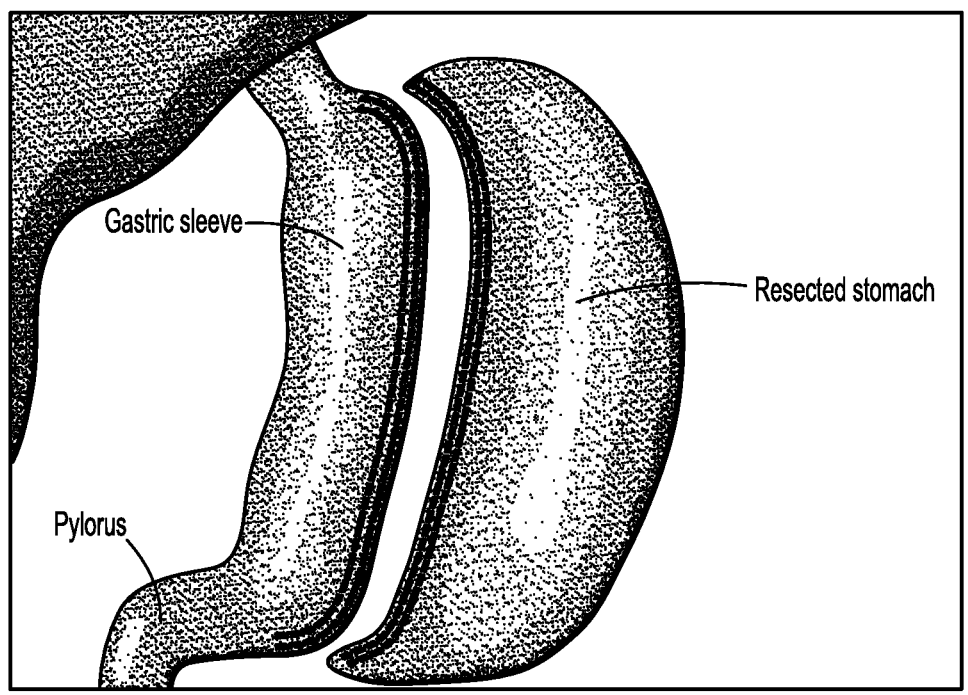
FIG. 1 schematically illustrates a patient's resected stomach as a result of a Natural Orifice Bariatric Procedure, in accordance with embodiments of the present disclosure.

Embodiments of the presently disclosed natural orifice bariatric procedure and apparatus for use therewith will now be described in detail with reference to the drawings wherein like reference numerals designate identical or corresponding elements in each of the several views. In the description that follows, the term "proximal", as is traditional, will refer to the end of the stapling device closest the operator and the term "distal" will refer to the end of the stapling device farthest from the operator.

Figure 2:
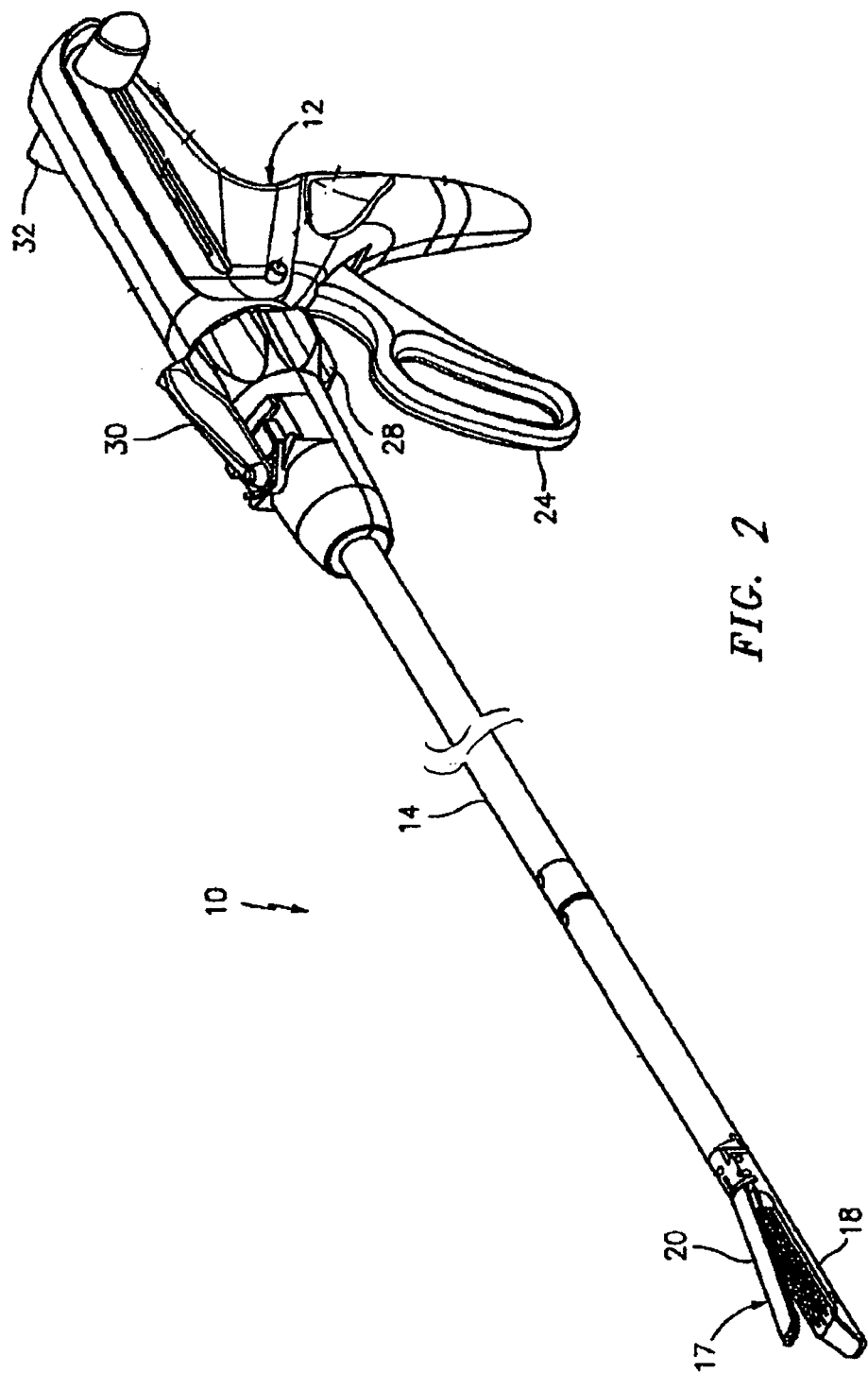
FIG. 2 is a perspective view of a surgical stapling instrument according to embodiments of the present disclosure.
Figure 3:
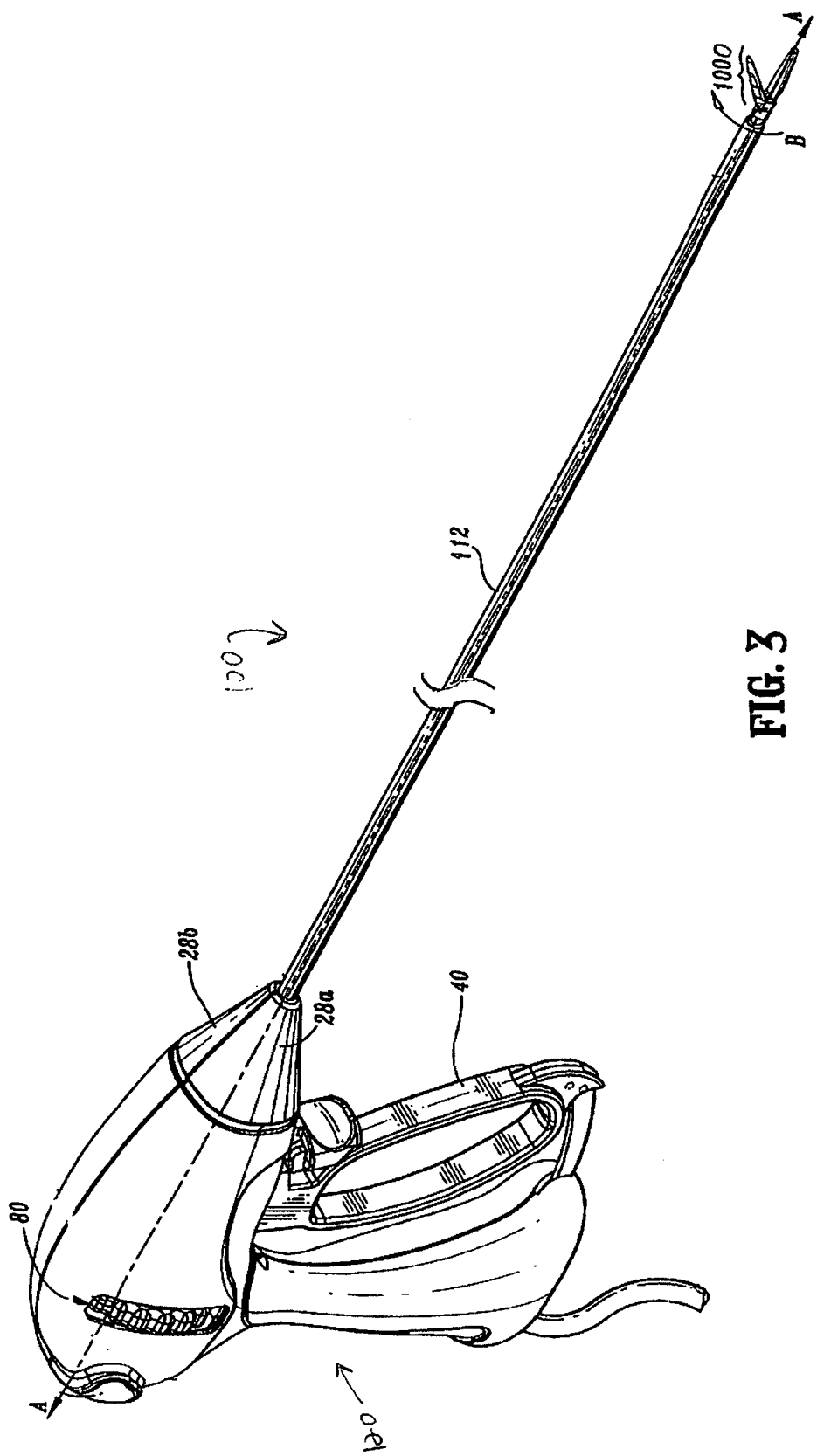
FIG. 3 is a perspective view of a vessel sealing instrument according to embodiments of the present disclosure.
Figure 4:
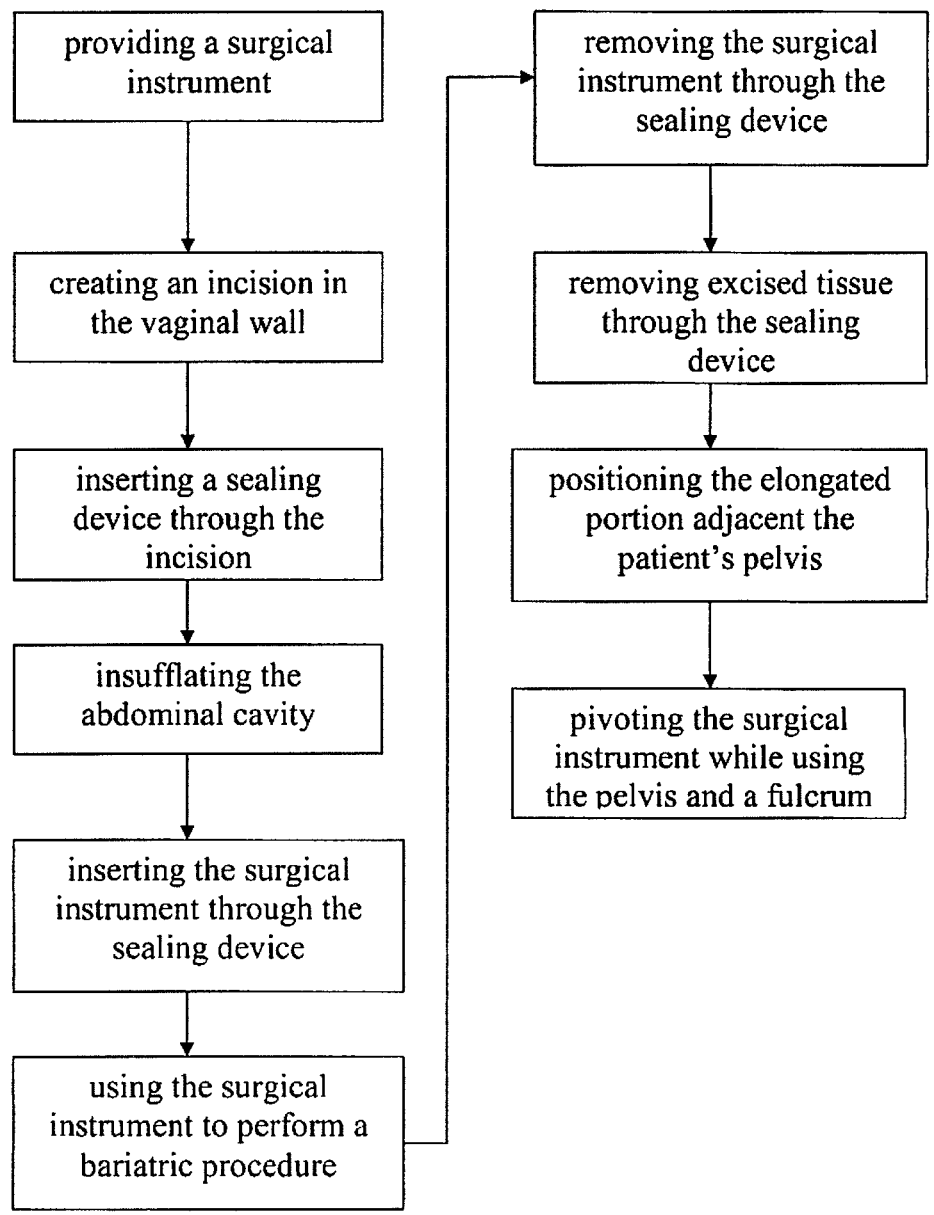
FIG. 4 is a flow chart representing steps of a method for performing a Natural Orifice Bariatric Procedure.

In the present disclosure, a surgical instrument is inserted through a natural orifice (e.g., vagina or rectum) of the patient, through an internal wall, and used to perform a surgical function. For example, a surgical stapler 10 may be inserted through the vaginal or rectal wall, advanced to the stomach, and used to staple and cut parts of the stomach to reduce the capacity of the stomach. Such a surgical stapler is described in U.S. Pat. No. 6,953,139 issued on Oct. 11, 2005 to Milliman et al., the entire contents of which are hereby incorporated by reference herein. FIG. 2 of the present disclosure illustrates an example of such a surgical stapler 10. Additionally, a vessel sealing instrument 100 may be inserted through the vaginal or rectal wall, advanced to the stomach, and used to fuse, seal and/or excise parts of the stomach to reduce the stomach's capacity. An example of a vessel sealing instrument is described in U.S. patent application Ser. No. 11/348,072, filed on Feb. 6, 2006 and entitled, "VESSEL SEALER AND DIVIDER HAVING A VARIABLE JAW CLAMPING MECHANISM," the entire contents of which are hereby incorporated by reference herein. FIG. 3 of the present disclosure illustrates an example of such a vessel sealing instrument 100.

Embodiments of the disclosed surgical stapling instrument 10, as shown in FIG. 2, include a handle portion 12 having at least one actuation mechanism disposed in mechanical cooperation therewith. The illustrated actuation mechanisms include a movable handle 24 (e.g., for affecting relative approximation between an anvil 20 and a cartridge assembly 18), a rotation knob 28 (e.g., for rotating the end effector 17 about the longitudinal axis defined by the elongated portion 14), an articulation knob 17 (e.g., for pivoting the end effector 17 with respect to the longitudinal axis), and a knife slide 32 (e.g., for affecting translation of a knife blade (not shown) between the jaw members).

Embodiments of the disclosed vessel sealing instrument 100, as shown in FIG. 3, include a handle portion 120 having at least one actuation mechanism disposed in mechanical cooperation therewith. The illustrated actuation mechanisms include a movable handle 40 (e.g., for affecting relative approximation between the two jaw members and/or for affecting a tissue seal), a rotation knob 28a, 28b (e.g., for rotating the end effector 1000 about the longitudinal axis A-A defined by the elongated portion 112), and an articulation wheel 80 (e.g., for pivoting the end effector 1000 in the general direction of arrow "B").

It is envisioned that the surgical instruments 10, 100 for use with the NOTES procedure of the present disclose have a longer endoscopic portion 14, 112 than the endoscopic portions of the devices disclosed in the incorporated references. The surgical instruments with an extended endoscopic portion of the present disclosure facilitate access to the stomach through the vagina or rectum. For instance, it is envisioned that the length of the surgical stapler 10 or vessel sealing instrument 100 used with the presently disclosed procedure may be between about 30 inches and about 45 inches long. Likewise, it is envisioned that the surgical stapler 10 of the present invention may have a length-to-diameter ratio of between about 63.5 to about 95 and that the vessel sealing instrument 100 may have a length-to-diameter ratio of between about 150 to about 230.

Previously described NOTES procedures require a surgical instrument with a flexible shaft to facilitate access to a desired surgical site via a curved path such as through the colon or trans-orally. Such flexible-shafted instruments have been difficult to control at remote surgical locations making performing precise surgical operations difficult. The endoscopic portion 14, 112 or shaft of the surgical instruments 10, 100 described herein for performing a NOTES procedure is substantially rigid. In the present disclosure, a surgical instrument 10, 100 having a substantially rigid shaft 14, 112 is preferable to provide greater control to the surgeon. Additionally, the non-flexible shafts 14, 112 of the instruments 10, 100 used to perform the procedure described herein allow direct access to the surgical site because of the orientation of the stomach with respect to the vagina and the rectum. That is, the stomach is generally in-line with the vaginal and rectal orifices, thus enabling access via an instrument 10, 100 with a non-flexible shaft 14, 112. Additionally, the presently described procedure utilizes the patient's pelvis as a fulcrum against which the rigid-shafted surgical instrument 10, 100 of the present disclosure can pivot against to affect a desired movement of the distal end (e.g., end effector 17, 1000) of the surgical instrument 10, 100.

It is also envisioned that the surgical instrument 10, 100 of the present disclosure includes a shaft 14, 112 that includes a substantially rigid portion and a flexible portion. For instance, it is contemplated that the distal portion of the surgical instrument 10, 100 is flexible or otherwise articulatable and the proximal portion of the surgical instrument, positionable adjacent the pelvis, is substantially rigid. Additionally, it is envisioned that the flexible portion is lockable in a desired orientation, e.g., along a curvilinear path.

A procedure of the present disclosure relating to performing a bariatric procedure on a female patient includes creating an incision in the vaginal wall (e.g., via a needle knife or a hot knife), inserting a sealing device to allow insufflation of the abdominal cavity, (e.g., a trocar or an endoscopy overtube), insufflating the abdominal cavity, inserting a surgical instrument 10, 100 through the sealing device, using the surgical instrument 10, 100 to perform a surgical task (e.g., a sleeve gastrectomy), removing the surgical instrument 10, 100 through the sealing device, and removing the excised tissue or organ (e.g., portion of the stomach) through the sealing device (e.g., via grasping the excised matter with a surgical stapler). Additionally, optional steps may include utilizing an anchoring device to help secure the sealing device within the incision, and inserting a visualization device (e.g., transrectally).

More particularly, a NOTES transvaginal sleeve gastrectomy procedure may be performed in the following steps. First, an incision is made in a female patient's vagina using a electrosurgical needle knife. The incision is next dilated using a standard dilation balloon. Next, an endoscopic over tube (e.g., overtube commercially available from US Endoscopy) is inserted into the incision and into the abdominal cavity. Insufflation is provided to the abdominal cavity via the overtube or via a needle placed through the abdominal cavity. Next, a vessel sealing device is inserted into the abdominal cavity via the vaginal incision and used to make an opening on the omentum on the greater curvature of the stomach. Once the lesser omental space is emptied, dissection continues cephalad close to the stomach wall. The dissection using the vessel sealing device terminates close to the gastroesophageal junction. Attention is paid to the short gastric vessels and preserving the spleen and to avoid bleeding from the capsule of the spleen or a branch of the splenic artery. Dissection of the hiatus is finished by dissecting to release the left crus and any avascular attachments from the posterior stomach to the pancreas. After the left part of the hiatus has been dissected, the greater curvature of the stomach is mobilized to within about 6 to 8 cm of the pylorus. Next, the vessel sealing device is removed from the vaginal incision and a surgical stapler as described herein is inserted into the abdominal cavity via the vaginal incision. The stapler is placed across the antrum and fired to start the sleeve gastrectomy. The stapler is withdrawn and the staple cartridge replaced. The stapler is reinserted in to the abdominal cavity. A 30-50 Fr. bougie may then be inserted through the esophagus into the stomach along the lesser curvature of the stomach to provide a guide for sizing the sleeve. Second and subsequent staple lines are fired through the stomach to seal the sleeve and transect the greater curvature of the stomach. The transected specimen is then removed via the vaginal incision. The overtube and any remaining devices are removed, and finally, the vaginal incision is closed.

A procedure of the present disclosure relating to performing a bariatric procedure on a female patient or a male patient includes the above steps, however the incision is created in a rectal wall.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

What is claimed:

1. A method of performing a bariatric procedure, the method comprising:

inserting a surgical instrument through a vaginal orifice of a patient such that an end effector of the surgical instrument is adjacent a portion of the patient's stomach;

positioning a portion of an elongated portion of the surgical instrument adjacent the patient's pelvis; and pivoting the surgical instrument while using the pelvis as a fulcrum.

2. The method of claim 1, further comprising performing a surgical task while the end effector of the surgical instrument is adjacent the portion of the patient's stomach.

3. The method of claim 2, wherein performing a surgical task includes performing one or more steps of a vertical sleeve gastrectomy procedure.

4. The method of claim 1, wherein inserting a surgical instrument includes inserting a surgical instrument having a length between about 30 inches and about 45 inches.

5. The method of claim 1, wherein inserting a surgical instrument includes inserting a stapling instrument.

6. The method of claim 5, wherein inserting a surgical instrument includes inserting a surgical stapling instrument having a length and a ratio of the length of the surgical stapling instrument to a diameter of the elongated portion is between about 63.5 and about 95.

7. The method of claim 1, wherein inserting a surgical instrument includes inserting a surgical instrument having an elongated portion that is non-flexible along its entire length.

8. The method of claim 1, wherein inserting a surgical instrument includes inserting a surgical instrument wherein a distal portion of the elongated portion is flexible and a proximal portion of the elongated portion is non-flexible.

9. A method of performing a transvaginal bariatric procedure, the method comprising:

creating an incision in a vaginal wall of a patient;

inserting at least a portion of a surgical instrument through the incision;

positioning a portion of an elongated portion of the surgical instrument adjacent a patient's pelvis; and pivoting the surgical instrument while using the pelvis as a fulcrum.

10. The method of claim 9, further comprising using the surgical instrument to perform a bariatric procedure.

11. The method of claim 9, wherein inserting at least a portion of a surgical instrument includes inserting a surgical instrument having a length between about 30 inches and about 45 inches.

12. The method of claim 9, wherein inserting at least a portion of a surgical instrument includes inserting a surgical instrument wherein an entire length of the elongated portion of the surgical instrument is non-flexible.

13. The method of claim 9, wherein inserting at least a portion of a surgical instrument includes inserting a surgical instrument wherein a distal portion of the elongated portion is flexible and a proximal portion of the elongated portion is non-flexible.

14. The method of claim 9, further comprising removing excised tissue through the incision in the vaginal wall.

15. The method of claim 9, further comprising positioning an end effector of the surgical instrument adjacent a portion of the patient's stomach.

* * * * *